(12) United States Patent
Kim et al.

(10) Patent No.: US 11,364,487 B2
(45) Date of Patent: Jun. 21, 2022

(54) CATALYST FOR OXYGEN-FREE DIRECT CONVERSION OF METHANE AND METHOD OF CONVERTING METHANE USING THE SAME

(71) Applicant: KOREA RESEARCH INSTITUTE OF CHEMICAL TECHNOLOGY, Daejeon (KR)

(72) Inventors: Yong Tae Kim, Daejeon (KR); Seok Ki Kim, Daejeon (KR); Hyun Woo Kim, Daejeon (KR); Sung Woo Lee, Daejeon (KR); Seung Ju Han, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 16/642,774

(22) PCT Filed: Oct. 23, 2018

(86) PCT No.: PCT/KR2018/012529
§ 371 (c)(1),
(2) Date: Feb. 27, 2020

(87) PCT Pub. No.: WO2019/146879
PCT Pub. Date: Aug. 1, 2019

(65) Prior Publication Data
US 2021/0077982 A1    Mar. 18, 2021

(30) Foreign Application Priority Data
Jan. 23, 2018   (KR) .................. 10-2018-0008155

(51) Int. Cl.
*B01J 23/745*   (2006.01)
*B01J 21/08*    (2006.01)
(Continued)

(52) U.S. Cl.
CPC ............. *B01J 23/745* (2013.01); *B01J 21/08* (2013.01); *B01J 35/026* (2013.01); *C07C 2/24* (2013.01);
(Continued)

(58) Field of Classification Search
None
See application file for complete search history.

(56) References Cited

U.S. PATENT DOCUMENTS

2014/0336432 A1   11/2014   Bao et al.
2016/0362351 A1   12/2016   Nagaki et al.

FOREIGN PATENT DOCUMENTS

| CN | 1247103 A | 3/2000 |
|----|-----------|--------|
| CN | 1532546 A | 9/2004 |

(Continued)

OTHER PUBLICATIONS

International Search Report of PCT/KR2018/012529, dated Apr. 5, 2019, English translation.
(Continued)

*Primary Examiner* — In Suk C Bullock
*Assistant Examiner* — Alyssa L Cepluch
(74) *Attorney, Agent, or Firm* — STIP Law Group, LLC

(57) ABSTRACT

The present invention relates to a catalyst for oxygen-free direct conversion of methane and a method of converting methane using the same, and more particularly to a catalyst for oxygen-free direct conversion of methane, in which the properties of the catalyst are optimized by adjusting the free space between catalyst particles packed in a reactor, thereby maximizing the catalytic reaction rate without precise control of reaction conditions for oxygen-free direct conversion of methane, minimizing coke formation and exhibiting stable catalytic performance even upon long-term operation, and to a method of converting methane using the same.

9 Claims, 2 Drawing Sheets

(51) Int. Cl.
  *B01J 35/02*   (2006.01)
  *C07C 2/76*    (2006.01)
  *C07C 2/24*    (2006.01)

(52) U.S. Cl.
  CPC ............ *C07C 2/76* (2013.01); *C07C 2521/08* (2013.01); *C07C 2523/745* (2013.01)

(56) References Cited

FOREIGN PATENT DOCUMENTS

| JP | 2015535830 A | 12/2015 | |
|----|----|----|----|
| WO | WO-2014183337 A1 * | 11/2014 | ............ B01J 23/745 |
| WO | WO2017062663 A1 | 4/2017 | |

OTHER PUBLICATIONS

Xiaoguang Guo et al, Direct, Nonoxidative Conversion of Methane to Ethylene, Aromatics, and Hydrogen, Science, May 9, 2014, pp. 616-619, vol. 344, American Association for the Advancement of Science, Washington DC, USA.

Mann Sakbodin et al, Hydrogen-Permeable Tubular Membrane Reactor: Promoting Conversion and Product Selectivity for Non-Oxidative Activation of Methane over an FecSiO2 Catalyst, Angewandte Chemie, 2016, pp. 16149-16152, vol. 55, Wiley-VCH Verlag GmbH & Co. KGaA, Weinheim, Germany.

Office Action from Korean Intellectual Property Office of 10-2018-0008155, dated Dec. 17, 2018.

* cited by examiner

CATALYST FOR OXYGEN-FREE DIRECT CONVERSION OF METHANE AND METHOD OF CONVERTING METHANE USING THE SAME

Cross-reference to Related Applications

This application is the U.S. National Phase under 35 U.S.C. § 371 of International Application No. PCT/KR2018/012529 filed on Oct. 23, 2018, which in turn claims the benefit of Korean Application No. 10-2018-0008155, filed on Jan. 23, 2018, the disclosures of which are incorporated by reference into the present application.

BACKGROUND OF THE INVENTION

1. Technical Field

The present invention relates to a catalyst for oxygen-free direct conversion of methane and a method of converting methane using the same, and more particularly to a catalyst for oxygen-free direct conversion of methane, which is capable of directly converting methane, which is a main component of natural gas, in an anaerobic or oxygen-free atmosphere, and to a method of converting methane using the same.

2. Description of the Related Art

Recently, many attempts have been made to convert methane ($CH_4$) obtainable from natural gas, shale gas and the like, into high-value-added products such as transport fuels or chemicals. Representative examples of high-value-added products obtainable from methane include light olefins (ethylene, propylene, butylene, etc.), and MTO (Methanol-to-Olefin) technology for producing light olefins via methanol from synthesis gas ($H_2$+CO) obtained through methane reforming and FTO (Fischer-Tropsch to Olefins) technology for directly producing light olefins from synthesis gas are known to be the most feasible production techniques. However, in the production of high-value-added products using synthesis gas, $H_2$ or CO is additionally required in order to remove O atoms from CO, which reduces the utilization efficiency of H or C atoms in the entire process.

Hence, there is a need for new technology capable of directly converting methane into high-value-added products without using synthesis gas. In order to directly convert methane into high-value-added products, activating methane by cleaving the strong C—H bonds (434 kJ/mol) in methane should be performed first. From this point of view, thorough research on oxidative coupling of methane (OCM) technology for activating methane using oxygen has been conducted. However, even during the OCM reaction, large amounts of thermodynamically stable $H_2O$ and $CO_2$ are formed due to the intense reactivity of $O_2$, thus lowering the utilization efficiency of H and C atoms, and thus there remains a problem.

With the goal of solving this problem, a technique for preparing ethylene, aromatics, etc. by direct conversion of methane under anaerobic or oxygen-free conditions has been recently developed, but is performed at high temperature and high pressure due to the low reactivity of methane, and the development of catalysts is essential. However, based on research results to date, a drastic decrease in catalytic activity owing to carbon (coke) deposition of catalysts under high-temperature and high-pressure conditions is highlighted as a key issue (Non-Patent Documents 0001 and 0002).

U.S. Patent Application Publication No. 2014/0336432 discloses a method of oxygen-free conversion of methane, including reacting a methane-containing methane feed in the presence of a catalyst in which metal elements are doped in the lattice of amorphous molten-state materials made from Si bonded with at least one of C, N and O in order to suppress carbon (coke) deposition of the catalyst under high-temperature and high-pressure conditions and also in which the amount of the catalyst that is doped in the metal lattice is 0.01 wt % to 10 wt % based on the total weight thereof. Moreover, U.S. Patent Application Publication No. 2016/0362351 discloses a method of oxygen-free coupling of methane using a catalyst in which chemically active metal is doped in the lattice of amorphous molten-state materials made from B, Al, Si, Ti, Zr and Ge bonded with at least one of C, N and O.

However, the above documents merely suggest a catalyst in which coke formation is suppressed and the catalytic reaction rate is improved, compared to a catalyst for oxygen-free direct conversion of methane prepared by a conventional sol-gel or impregnation process, and do not provide a catalyst optimized for oxygen-free direct conversion of methane. Moreover, in order to maximize a high catalytic reaction rate and simultaneously minimize coke formation, a reactor suitable for the radical reaction has to be additionally provided, and also, the reaction conditions must be precisely controlled in consideration of the type of catalyst that is applied to the oxygen-free direct conversion of methane. Furthermore, in the case in which the reaction conditions are not appropriate, the coke selectivity may increase with an increase in the methane conversion rate, and thus hydrocarbon selectivity, production rate, etc. are lowered, which is undesirable. In addition, because many factors affect the reaction, such as the location of a catalyst-packed portion, the reactor material, the impurity content in a reaction system and the purity of a methane feed, it is difficult to control the hydrocarbon selectivity, production rate, etc.

CITATION LIST

Patent Literature (Patent Document 1) U.S. Patent Application Publication No. 2014/0336432 (Publication Date: Nov. 13, 2014)
(Patent Document 2) U.S. Patent Application Publication No. 2016/0362351 (Publication Date: Dec. 15, 2016)

Non-Patent Literature (Non-Patent Document 1) X, Guo et al., Direct, Nonoxidative Conversion of Methane to Ethylene, Aromatics, and Hydrogen, Science, 344, 2014, 616 to 619
(Non-Patent Document 2) Mann Sakbodin et al., Hydrogen-Permeable Tubular Membrane Reactor: Promoting Conversion and Product Selectivity for Non-Oxidative Activation of Methane over an FeVSiO2 Catalyst, Angew. Chem. 2016, 128, 16383 to 16386

SUMMARY OF THE INVENTION

Accordingly, the present invention has been made keeping in mind the problems encountered in the related art, and an objective of the present invention is to provide a catalyst for oxygen-free direct conversion of methane, in which the physicochemical properties of the catalyst may be optimized without precise control of direct conversion reaction conditions of methane, thus maximizing a catalytic reaction rate, minimizing coke formation, and exhibiting stable catalytic performance even upon long-term operation, and a method of converting methane using the same.

In order to accomplish the above objective, an embodiment of the present invention provides a catalyst for oxygen-free direct conversion of methane, which is granulated and packed in the form of a shaped catalyst body in a reactor for oxygen-free direct conversion of methane, in which the catalyst satisfies Mathematical Formula 1 below.

$$(V_{inter}/V_{void}) \leq 0.4 \quad \text{[Mathematical Formula 1]}$$

In Mathematical Formula 1, $V_{void}$ is $V_R-V_A$ ($V_R$ is the volume of the catalyst-packed portion in the reactor, and $V_A$ is the apparent volume of the shaped catalyst body packed in the catalyst-packed portion), and $V_{inter}$ is the interparticle space volume of the shaped catalyst body packed in the catalyst-packed portion.

In a preferred embodiment of the present invention, the ratio $[(V_{void}+V_{inter})/VR]$ of $V_{void}$ and $V_{inter}$ to $V_R$ of the catalyst is 0.7 or less.

In a preferred embodiment of the present invention, the sum of $V_{void}$ and $V_{inter}$ of the catalyst is 0.7 ml/$g_{cata.}$ or less.

In a preferred embodiment of the present invention, the $V_{inter}$ of the catalyst is 0.2 ml/$g_{cata.}$ or less.

In a preferred embodiment of the present invention, the catalyst includes a catalyst carrier including silicon oxide and iron dispersed and supported in a monoatomic form on the catalyst carrier.

In a preferred embodiment of the present invention, the amount of iron that is supported is 0.1 wt % to 10.0 wt % based on the total weight of the catalyst.

In a preferred embodiment of the present invention, the catalyst carrier is in a crystalline molten state.

In a preferred embodiment of the present invention, the interparticle space volume $V_{inter}$ of the shaped catalyst body in which the catalyst is granulated is decreased through repeated fusing and solidification.

Another embodiment of the present invention provides a method of converting methane including reacting methane in an anaerobic or oxygen-free atmosphere using the above catalyst.

In a preferred embodiment of the present invention, the reacting is carried out at a temperature of 950° C. to 1100° C.

According to the present invention, the catalyst for oxygen-free direct conversion of methane is configured such that the physicochemical properties of the catalyst can be optimized by controlling the free space between catalyst particles packed in the reactor, thereby maximizing the catalytic reaction rate without precise control of reaction conditions for oxygen-free direct conversion of methane, minimizing coke formation, and exhibiting stable catalytic performance even upon long-term operation.

DESCRIPTION OF SPECIFIC EMBODIMENTS

Figure 1:
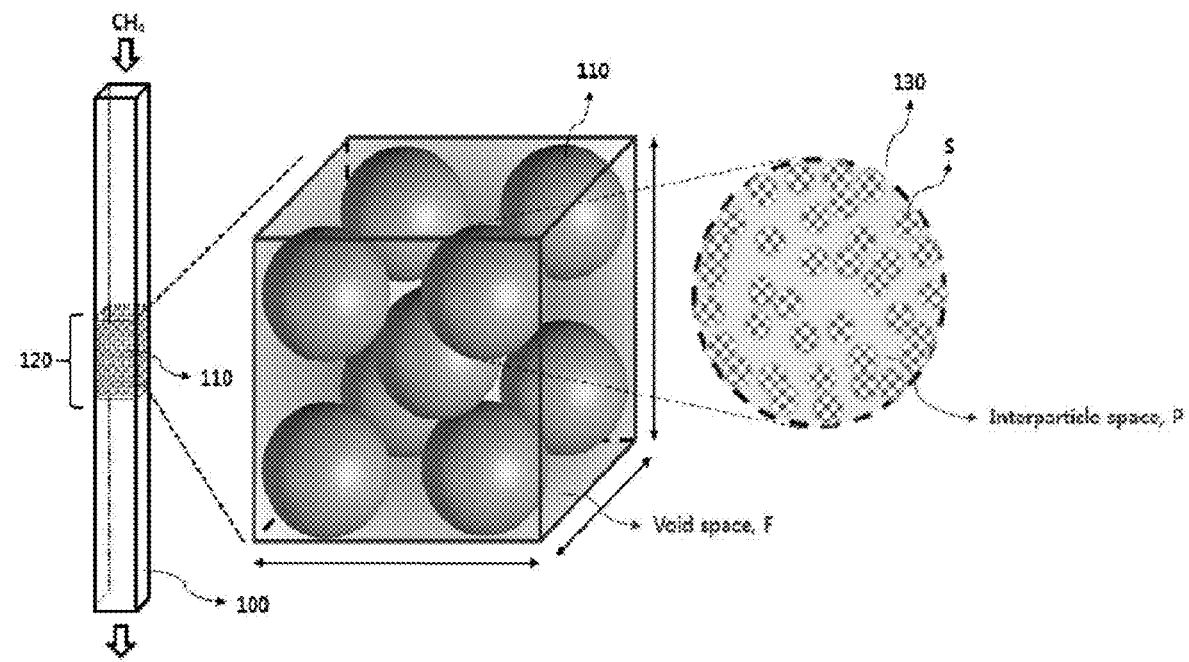
FIG. 1 schematically shows a catalyst for oxygen-free direct conversion of methane, which is packed in a reactor, according to an embodiment of the present invention.

Unless otherwise defined, all technical and scientific terms used herein have the same meanings as those typically understood by those skilled in the art to which the present invention belongs. Generally, the nomenclature used herein is well known in the art and is typical.

As used herein, when any part is said to "include" any element, this does not mean that other elements are excluded, and such other elements may be further included unless otherwise specifically mentioned.

As used herein, the term "free space $V_{free\ space}$" means the remaining space of a catalyst-packed portion except the solid phase of a shaped catalyst body (bodies) when the catalyst-packed portion is formed in a reactor by packing the shaped catalyst body (bodies) resulting from granulating a catalyst in the reactor, and has a meaning including the interparticle space $V_{inter}$ of the shaped catalyst body (bodies) including closed pores and open pores in the packed shaped catalyst body (bodies); and the void space $V_{void}$ of the catalyst-packed portion except the space occupied by the shaped catalyst body (bodies) including closed pores and open pores.

As used herein, "shaped catalyst body (bodies)" means one or more shaped catalyst bodies, in which the number of shaped catalyst bodies packed in the catalyst-packed portion may be 1 or more. Hereinafter, the term "shaped catalyst body", is used, and is to be interpreted to have the same meaning as "shaped catalyst body (bodies)".

As used herein, the term "packing density" refers to the volume of the catalyst-packed portion relative to the weight of the shaped catalyst body packed in the reactor.

As used herein, the term "apparent volume $V_A$ of a shaped catalyst body" refers to the volume of the shaped catalyst body including all of closed pores and open pores, and the term "true volume $V_P$ of a shaped catalyst body" refers to the substantial volume of the shaped catalyst body, that is, the volume of the solid phase of the shaped catalyst body.

As used herein, the term "supported in a monoatomic form" means that iron, which is a catalyst active material, is dispersed on an atomic basis on a carrier, which is distinguished from the dispersion of iron nanoparticles, formed by agglomeration of iron atoms, on a catalyst carrier.

An aspect of the present invention pertains to a catalyst for oxygen-free direct conversion of methane, which is granulated and packed in the form of a shaped catalyst body in a reactor for oxygen-free direct conversion of methane, the catalyst satisfying Mathematical Formula 1 below.

$$(V_{inter}/V_{void}) \leq 0.4 \quad \text{[Mathematical Formula 1]}$$

In Mathematical Formula 1, $V_{void}$ is $V_R-V_A$ ($V_R$ is the volume of the catalyst-packed portion in the reactor, and $V_A$ is the apparent volume of the shaped catalyst body packed in the catalyst-packed portion), and $V_{inter}$ is the interparticle space volume of the shaped catalyst body packed in the catalyst-packed portion.

The present inventors have diligently tried to develop catalysts capable of maximizing the catalytic reaction rate during the oxygen-free direct conversion of methane, minimizing coke formation and exhibiting stable catalytic performance even upon long-term operation, and have ascertained that, even when catalysts composed of the same composition are used, the packing density and free space thereof may vary depending on the catalyst preparation method, the catalyst active component, the amount of the catalyst active component, etc., and the reaction rate and coke deposition may be affected by the packing density of the catalyst and free space, thus culminating in the present invention.

Hereinafter, a detailed description will be given of the present invention with reference to the accompanying drawings.

FIG. 1 schematically shows the catalyst packed in the reactor. In order to directly convert methane into a hydrocarbon compound such as an olefin, an aromatic compound, etc. in an anaerobic or oxygen-free atmosphere, a catalyst 130 is granulated and packed in the form of a shaped catalyst body 110 in a reactor 100 for oxygen-free direct conversion of methane.

The reactor for oxygen-free direct conversion of methane is any reactor capable of being packed with a solid catalyst (a shaped catalyst body) useful in the oxygen-free direct conversion of methane, and examples thereof may include, but are not limited to, a tubular reactor, a slab reactor, a microchannel reactor, a fluidized-bed reactor and the like.

When the shaped catalyst body 110 is packed in the reactor 100, a catalyst-packed portion 120 is formed in the reactor. The shaped catalyst body is configured such that catalyst particles are formed in a specific structure through physical bonding, and the shaped catalyst body may be prepared through a typical process in the art. One or more shaped catalyst bodies may be packed in the reactor depending on the shape thereof, and the shape of the shaped catalyst body may be easily adjusted depending on the reactor structure, reaction environment, reaction conditions and the like. Examples of the shaped catalyst body may include, but are not limited to, a pellet, monolith, thin film, and the like.

In the catalyst-packed portion 120, space except the solid phase S of the shaped catalyst body, that is, free space, is formed, and the free space may include the interparticle space (P) volume $V_{inter}$ of the shaped catalyst body including closed pores and open pores in the packed shaped catalyst body, and the void space volume $V_{void}$ of the catalyst-packed portion 120 except the apparent volume $V_A$ of the shaped catalyst body, which is the volume of the shaped catalyst body including the above pores.

Specifically, the free space of the catalyst-packed portion in the reactor may be represented as the sum of the interparticle space volume $V_{inter}$ of the shaped catalyst body packed in the catalyst-packed portion 120 and the void space volume $V_{void}$ of the catalyst-packed portion except the apparent volume of the shaped catalyst body.

As for the oxygen-free direct conversion of methane, radical-based gas-phase reaction and catalytic reaction are carried out simultaneously on the surface of the shaped catalyst body in which the catalyst is granulated and in the free space, and thus, when the surface of the shaped catalyst body and the free space are controlled, the reaction rate and coke deposition may be adjusted.

The catalyst for oxygen-free direct conversion according to the present invention may satisfy the conditions defined by Mathematical Formula 1.

When the interparticle space volume $V_{inter}$ of the shaped catalyst body packed in the catalyst-packed portion is greater than the void space volume $V_{void}$ of the catalyst-packed portion except the apparent volume $V_A$ of the shaped catalyst body, the radical-based gas-phase reaction is affected by the catalyst surface, thus facilitating coke formation, which is undesirable. Hence, it is preferred that the interparticle space volume $V_{inter}$ of the shaped catalyst body packed in the catalyst-packed portion be equal to or smaller than the void space volume $V_{void}$ of the catalyst-packed portion except the apparent volume of the shaped catalyst body. According to the present invention, it was confirmed that the gas-phase reaction of methane into coke occurred in the interparticle space volume $V_{inter}$ of the packed shaped catalyst body, rather than the void space volume $V_{void\ between\ shaped\ catalyst\ bodies}$.

In the catalyst for oxygen-free direct conversion according to the present invention, the ratio ($V_{inter}/V_{void}$) of the interparticle space volume $V_{inter}$ of the shaped catalyst body packed in the catalyst-packed portion to the void space volume $V_{void}$ of the catalyst-packed portion except the apparent volume of the shaped catalyst body is 0.4 or less. If the $V_{inter}/V_{void}$ ratio exceeds 0.4, the radical-based gas-phase reaction, which is affected by the catalyst surface, is mainly carried out, undesirably resulting in high coke selectivity.

In the catalyst for oxygen-free direct conversion according to the present invention, moreover, the ratio $[(V_{free\ space})/V_R]$ of the free space volume $[(V_{free\ space}; (V_{void}+V_{inter})]$ to the volume $V_R$ of the catalyst-packed portion 120 is 0.7 or less, and preferably 0.6 or less. If the ratio of the free space volume to the volume $V_R$ of the catalyst-packed portion exceeds 0.7, there may occur a problem of increased coke selectivity during the reaction due to increased probability of the radicals generated on the catalyst surface being converted in a gas phase.

Here, the amount of free space in the shaped catalyst body packed in the reactor may be 0.7 ml/$g_{cata.}$ or less, and preferably 0.55 ml/$g_{cata.}$ or less. If the free space in the catalyst-packed portion exceeds 0.7 ml/$g_{cata.}$, there may occur a problem of increased coke selectivity during the reaction due to increased probability of the radicals generated on the catalyst surface being excessively converted in a gas phase.

The volume $V_R$ of the catalyst-packed portion of the reactor may be measured through the packing density of the shaped catalyst body and the weight of the shaped catalyst body present in the reactor, and the intrinsic density, apparent volume $V_A$ and true volume $V_P$ of catalyst particles may be measured using a pycnometer. The free space of the catalyst-packed portion may be calculated by subtracting the true volume $V_P$ of the catalyst particles from the volume $V_R$ of the catalyst-packed portion. The void space $V_{void}$ between shaped catalyst bodies may be calculated using a random loose packing process [Physical Review E 74, 031309 (2006)]. The interparticle space volume $V_{inter}$ of the catalyst may be calculated by subtracting the void space $V_{void}$ between the shaped catalyst bodies from the free space volume of the catalyst-packed portion.

As described above, the catalyst satisfying the packing density and free space conditions includes a catalyst carrier including silicon oxide and iron dispersed and supported in a monoatomic form on the catalyst carrier.

The catalyst is configured such that the crystalline molten-state silicon oxide lattice is doped with iron as a catalyst active component, in which two C atoms and one Si atom are bound to a single Fe atom and embedded in a silicon oxide base, and the catalyst may be obtained by doping the lattice of silicon oxide as the catalyst carrier with iron (Fe), followed by fusing and solidification.

The catalyst is formed into a shaped catalyst body by uniformly mixing and fusing the catalyst carrier and the catalyst active component, whereby the interparticle space volume $V_{inter}$ of the shaped catalyst body packed in the catalyst-packed portion is small, thus exhibiting a high methane conversion rate and high hydrocarbon selectivity and suppressing coke formation.

In the catalyst for oxygen-free direct conversion of methane according to the present invention, the amount of iron (Fe) is adjusted before fusing of the catalyst, whereby the interparticle space volume $V_{inter}$ of the shaped catalyst body packed in the catalyst-packed portion may be lowered. Iron (Fe) acts as a dopant upon fusing of the catalyst, thus adjusting the microstrain of the catalyst carrier, ultimately decreasing the interparticle space volume $V_{inter}$ of the shaped catalyst body.

The amount of iron that is supported as the catalyst active component is 0.1 wt % to 10.0 wt %, and preferably 0.3 wt % to 10.0 wt %, based on the total weight of the catalyst. If the amount of iron that is supported is less than 0.1 wt % based on the total weight of the catalyst, the small amount of iron capable of acting as a dopant makes it difficult to adjust the interparticle space volume of the shaped catalyst body. On the other hand, if the amount thereof exceeds 10.0 wt %, the amount of iron particles, as the active sites for methane activation, may increase, undesirably increasing the formation rate of coke.

The catalyst may be prepared by uniformly mixing and fusing the catalyst carrier and the catalyst active component. Here, a ball mill may be used to decrease the interparticle space volume $V_{inter}$ of the shaped catalyst body and to maximize the activity of the active component. The particle size of the catalyst carrier and the catalyst active component (Fe) upon fusing is 50 μm or less, and preferably 50 nm to 50 μm. If the particle size of the catalyst carrier and the catalyst active component (Fe) exceeds 50 μm, adjusting the interparticle space volume of the shaped catalyst body (bodies) during catalyst fusing is limited, and moreover, the amount of iron nanoparticles as the catalyst active component may increase, undesirably increasing the formation rate of coke. In order to decrease the particle size of the catalyst carrier and the catalyst active component to 1 μm or less, a wet ball mill is used. As the solvent therefor, any solvent may be used without limitation, so long as it is a material that does not change the oxidation state of the catalyst carrier and the catalyst active component, and preferable examples of the solvent include methanol, ethanol, propanol, butanol, and the like.

As the method of preparing the catalyst, any method may be used without limitation, so long as it is able to prepare a catalyst in which the catalyst carrier and the catalyst active component are uniformly mixed and fused and thus the interparticle space volume $V_{inter}$ of the shaped catalyst body packed in the catalyst-packed portion is small, and preferable examples thereof include chemical vapor deposition (CVD), vapor axis deposition (VAD), laser-assisted organic chemical vapor deposition (LCVD), sol-gel processing, porous Si-compound impregnation, etc.

Specifically, chemical vapor deposition (CVD) enables the preparation of a catalyst by reacting a carrier gas such as nitrogen, helium or argon, a silicon precursor and an iron precursor with water vapor, fusing the reaction product in ambient air, inert gas or a vacuum, and solidifying the fused product.

Vapor phase axis deposition (VAD) enables the preparation of a catalyst by reacting a silicon precursor and an iron precursor, transferred using $H_2$, with water vapor, depositing the reaction product on the surface of a high-temperature device (i.e. at least one of corundum, silicon carbide and silicon nitride), followed by fusing in ambient air, inert gas or a vacuum and solidification of the fused product.

Laser-assisted organic chemical vapor deposition (LCVD) enables the preparation of a catalyst by reacting a carrier gas such as nitrogen, helium or argon, a silicon precursor and an iron precursor with water vapor through laser activation using a laser as a heat source, fusing the reaction product in ambient air, inert gas or a vacuum, and solidifying the fused product.

Sol-gel processing enables the preparation of a catalyst by dissolving a silicon precursor and an iron precursor in a solvent such as water, performing a hydrolysis and condensation reaction, drying the reaction product, fusing the dried reaction product in ambient air, inert gas or a vacuum, and solidifying the fused product.

Porous Si-compound impregnation enables the preparation of a catalyst by impregnating a catalyst carrier comprising a porous solid silicon precursor (at least one of silica, silicon carbide and silicon nitride) with an iron precursor, followed by drying, fusing in ambient air, inert gas or a vacuum, and solidification of the fused product.

Examples of the silicon precursor may include gas, liquid and solid silicon precursors. Here, the liquid silicon precursor may include tetraethyl silicate, silicon tetrachloride, organosilane, and the like, and the solid silicon precursor may include silica, silicon carbide, silicon nitride, and the like.

The iron precursor may include iron oxide such as FeO, $Fe_2O_3$, $Fe_3O_4$, etc., iron carbide such as $Fe_5C_2$, $Fe_3C$, etc., iron nitride such as $Fe_2N$, $Fe_4N$, $Fe_7N_3$, etc., iron silicide and iron silicate such as $Fe_2SiO_4$, $Fe_2O_3 \cdot SiO_2$, etc., and the like.

The crystal structure of the catalyst carrier prepared by the above method is α-cristobalite, characterized in that it is reversibly transformed into β-cristobalite when heated to 200° C. to 300° C.

These methods of preparing the catalyst include different processes from each other, but include a fusing step and a solidification step. The fusing step aims to release the —OH group when doping silicon oxide with the iron element and to decrease the interparticle space volume $V_{inter}$ of the shaped catalyst body packed in the catalyst-packed portion, and the fusing step may be conducted at 1,200° C. to 3,000° C. in ambient air, inert gas or a vacuum. If the temperature of the fusing step is lower than 1200° C., it is difficult to fuse the catalyst carrier and the catalyst active component and thus the preparation of a uniform catalyst may become problematic. On the other hand, if the temperature thereof is higher than 3000° C., loss of the catalyst carrier and the catalyst active component may occur due to vaporization thereof, causing problems in the preparation of a uniform catalyst.

After the fusing step, the solidification step may be performed through rapid cooling or natural cooling. The rapid cooling may be conducted through gas cooling, water cooling, oil cooling, liquid nitrogen cooling, and the like, and preferably raid cooling is carried out at a rate of 1° C./min to $10^{0°}$ C./min.

The gas in the gas cooling may be at least one selected from the group consisting of inert gas and air, and in the oil cooling, the oil may be mineral oil, canola oil, silicone oil, or the like.

In the preparation of the catalyst for oxygen-free direct conversion of methane according to the present invention, the fusing step and the solidification step may be repeated, whereby the interparticle space volume $V_{inter}$ of the shaped catalyst body packed in the catalyst-packed portion may be further reduced. Here, the number of times that the fusing step and the solidification step are repeated is 2 or more, and preferably 2 to 5.

The catalyst for oxygen-free direct conversion of methane thus prepared is uniformly mixed with an inorganic binder, an organic binder, water, etc. in order to granulate the same, thus obtaining a catalyst mixture, which is then shaped to produce a shaped catalyst body.

The organic binder is not particularly limited, so long as it is one commonly used in the art, and at least one selected from among methyl cellulose, ethylene glycol, polyol, food oil and organic fatty acid is preferably used. Specific examples of the organic binder preferably include hydroxymethyl cellulose and polyvinyl alcohol. The inorganic binder is not particularly limited, so long as it is one commonly used in the art, and at least one selected from among solid silica, solid alumina, solid silica-alumina, silica sol, alumina sol, and water glass is preferably used. Specific examples of the inorganic binder preferably include fumed silica, silica sol, boehmite and alumina sol.

The catalyst mixture is typically formed into a shaped catalyst body by coating a catalyst structure such as a honeycomb structure or a monolith structure with the catalyst mixture, or by directly extruding the catalyst component of the catalyst mixture. Here, coating and extrusion of the catalyst mixture may be easily performed through any method used in the art, and a detailed description thereof will be omitted.

One or more shaped catalyst bodies may be packed in the catalyst-packed portion in the reactor for oxygen-free direct conversion of methane, depending on the shape of the shaped catalyst body. The process of packing the shaped catalyst body may also be easily performed through any process used in the art.

Another aspect of the present invention pertains to a method of converting methane including reacting methane in an anaerobic or oxygen-free atmosphere using the catalyst for oxygen-free direct conversion of methane described above.

The method of converting methane according to the present invention may include reacting methane with an inert gas and/or a non-inert gas at a high temperature in the presence of the catalyst to afford an olefin or aromatic compound.

Specifically, the catalyst according to the present invention is shaped, and the shaped catalyst body thus obtained is located in the catalyst-packed portion of the reactor, after which methane, inert gas and/or non-inert gas are introduced thereto.

The methane is introduced in a relative amount of 80 to 100% (v/v), and preferably 90 to 100% (v/v), based on the total gas volume introduced into the reactor, and the inert gas and/or the non-inert gas are introduced in relative amounts of 20% (v/v) or less, and preferably 10% (v/v) or less, based on the total gas volume.

The inert gas and the non-inert gas function to stabilize and maintain the reaction state. The inert gas may be nitrogen, helium, neon, argon, or krypton, and the non-inert gas may be carbon monoxide, hydrogen, carbon dioxide, water, monohydric alcohol (1 to 5 carbon atoms), dihydric alcohol (2 to 5 carbon atoms), or alkanes (2 to 8 carbon atoms).

The reaction temperature is 900° C. to 1150° C., and particularly 1000° C. to 1100° C., and the reaction pressure is 0.1 bar to 10 bar, and preferably 0.1 bar to 5 bar. These conditions are determined taking into consideration the hydrocarbon selectivity and yield, and may maximize the selectivity from methane to hydrocarbons. Here, the coke formation may be minimized under the above conditions, thereby minimizing the pressure drop due to coke formation and the carbon efficiency due to coke formation during the reaction.

If the reaction temperature is lower than 900° C., the generation rate of radicals is low due to methane activation, thus lowering the energy efficiency. On the other hand, if the reaction temperature is higher than 1150° C., a problem in which the retention time of methane in the reactor has to be minimized in order to suppress coke formation may arise.

The product of direct conversion of methane may be a hydrocarbon including paraffin, olefin or alkyne, such as ethane, ethylene, acetylene, propylene, butylene, etc., or an aromatic compound such as benzene, toluene, xylene, ethylbenzene, or naphthalene.

The method of converting methane according to the present invention is capable of inducing methane activity without precise control of reaction conditions, and is effective at maintaining a stable hydrocarbon yield even upon long-term operation.

A better understanding of the present invention will be given through the following examples. These examples are merely set forth to illustrate the present invention but are not to be construed as limiting the scope of the present invention.

Example 1

A mixed solution comprising 375 ml of toluene and 175 ml of methanol was refluxed in an argon atmosphere to remove dissolved oxygen therefrom, and 8.7 g of $FeCl_2$ was added thereto and dissolved. Then, 9.3 g of $NaOC_2H_5$ was added thereto and a sol-gel reaction was carried out, and 7.9 g of TEOS (tetraethoxysilane) and 10 ml of 0.2 M NaOH were added under reflux conditions and then refluxed for 12 hr. The resulting gel was dried in a rotary evaporator for 3 hr, fired at 800° C. for 2 hr in a nitrogen atmosphere, and washed with deionized water and methanol, thus obtaining fayalite ($Fe_2SiO_4$). 0.112 g of the fayalite thus obtained was subjected to ball milling (250 rpm) with 6 g of quartz particles for 15 hr in an Ar atmosphere and fused at 1700° C. for 6 hr in ambient air to afford a fused catalyst (1 wt % $Fe@SiO_2$) containing 1.0 wt % of iron supported thereon. 6 g of the 1 wt % $Fe@SiO_2$ thus obtained was additionally mixed with 0.112 g of fayalite, subjected to ball milling for 15 hr in an Ar atmosphere, and fused at 1700° C. for 6 hr in ambient air, thus preparing a catalyst (2 wt % Fe—$Fe@SiO_2$) containing 2.0 wt % of iron supported thereon for oxygen-free direct conversion of methane. The catalyst for oxygen-free direct conversion of methane thus obtained was formed into a pellet-shaped catalyst body having a diameter of 630 m using a pelletizer.

Example 2

A mixed solution comprising 375 ml of toluene and 175 ml of methanol was refluxed in an argon atmosphere to remove dissolved oxygen therefrom, and 8.7 g of $FeCl_2$ was added thereto and dissolved. Then, 9.3 g of $NaOC_2H_5$ was added thereto and a sol-gel reaction was carried out, and 7.9 g of TEOS and 10 ml of 0.2 M NaOH were added under reflux conditions and then refluxed for 12 hr. The resulting gel was dried in a rotary evaporator for 3 hr, fired at 800° C. for 2 hr in a nitrogen atmosphere, and washed with deionized water and methanol, thus obtaining fayalite ($Fe_2SiO_4$).

0.0112 g of the fayalite thus obtained was subjected to ball milling (250 rpm) with 6 g of quartz particles for 15 hr in an Ar atmosphere, and fused at 1700° C. for 6 hr in ambient air, thus preparing a catalyst (0.1 wt % Fe—Fe@SiO$_2$) containing 0.1 wt % of iron supported thereon for oxygen-free direct conversion of methane. The catalyst for oxygen-free direct conversion of methane thus obtained was formed into a pellet-shaped catalyst body having a diameter of 630 μm using a pelletizer.

Example 3

A catalyst for oxygen-free direct conversion of methane was prepared in the same manner as in Example 2, with the exception that the amount of fayalite was changed to 0.056 g to afford a catalyst containing 0.5 wt % of iron supported thereon for oxygen-free direct conversion of methane. The catalyst for oxygen-free direct conversion of methane thus obtained was formed into a pellet-shaped catalyst body having a diameter of 630 μm using a pelletizer.

Example 4

A catalyst for oxygen-free direct conversion of methane was prepared in the same manner as in Example 2, with the exception that the amount of fayalite was changed to 0.112 g to afford a catalyst containing 1.0 wt % of iron supported thereon for oxygen-free direct conversion of methane. The catalyst for oxygen-free direct conversion of methane thus obtained was formed into a pellet-shaped catalyst body having a diameter of 630 μm using a pelletizer.

Example 5

A catalyst for oxygen-free direct conversion of methane was prepared in the same manner as in Example 2, with the exception that the amount of fayalite was changed to 0.224 g to afford a catalyst containing 2 wt % of iron supported thereon for oxygen-free direct conversion of methane. The catalyst for oxygen-free direct conversion of methane thus obtained was formed into a pellet-shaped catalyst body having a diameter of 630 μm using a pelletizer.

Example 6

A catalyst for oxygen-free direct conversion of methane was prepared in the same manner as in Example 2, with the exception that the amount of fayalite was changed to 1.12 g to afford a catalyst containing 10.0 wt % of iron supported thereon for oxygen-free direct conversion of methane. The catalyst for oxygen-free direct conversion of methane thus obtained was formed into a pellet-shaped catalyst body having a diameter of 630 μm using a pelletizer.

Comparative Example 1

0.0369 g of Fe(NO$_3$)$_3$.9H$_2$O was added to 50 ml of deionized water (DI water) and dissolved. Then, 5 g of SiO$_2$ was added thereto and stirred at 60° C. for 6 hr at 120 rpm. The DI water remaining therein was removed under reduced pressure, followed by drying at 110° C. for 12 hr. The resulting material was fired at 550° C. for 4 hr, thus preparing a catalyst (0.1 wt % Fe/SiO$_2$) containing 0.1 wt % of iron supported thereon for oxygen-free direct conversion of methane. The catalyst for oxygen-free direct conversion of methane thus obtained was formed into a pellet-shaped catalyst body having a diameter of 630 μm using a pelletizer.

Comparative Example 2

A catalyst for oxygen-free direct conversion of methane was prepared in the same manner as in Comparative Example 1, with the exception that the amount of Fe(NO$_3$)$_3$.9H$_2$O was changed to 0.1111 g to afford a catalyst (0.3 wt % Fe/SiO$_2$) containing 0.3 wt % of iron supported thereon for oxygen-free direct conversion of methane. The catalyst for oxygen-free direct conversion of methane thus obtained was formed into a pellet-shaped catalyst body having a diameter of 630 μm using a pelletizer.

Comparative Example 3

A catalyst for oxygen-free direct conversion of methane was prepared in the same manner as in Comparative Example 1, with the exception that the amount of Fe(NO$_3$)$_3$.9H$_2$O was changed to 0.1855 g to afford a catalyst (0.5 wt % Fe/SiO$_2$) containing 0.5 wt % of iron supported thereon for oxygen-free direct conversion of methane. The catalyst for oxygen-free direct conversion of methane thus obtained was formed into a pellet-shaped catalyst body having a diameter of 630 μm using a pelletizer.

≤Comparative Example 4

A catalyst for oxygen-free direct conversion of methane was prepared in the same manner as in Comparative Example 1, with the exception that the amount of Fe(NO$_3$)$_3$.9H$_2$O was changed to 0.3728 g to afford a catalyst (1.0 wt % Fe/SiO$_2$) containing 1.0 wt % of iron supported thereon for oxygen-free direct conversion of methane. The catalyst for oxygen-free direct conversion of methane thus obtained was formed into a pellet-shaped catalyst body having a diameter of 630 μm using a pelletizer.

Comparative Example 5

A catalyst for oxygen-free direct conversion of methane was prepared in the same manner as in Comparative Example 1, with the exception that the amount of Fe(NO$_3$)$_3$.9H$_2$O was changed to 1.9426 g to afford a catalyst (5.0 wt % Fe/SiO$_2$) containing 5.0 wt % of iron supported thereon for oxygen-free direct conversion of methane. The catalyst for oxygen-free direct conversion of methane thus obtained was formed into a pellet-shaped catalyst body having a diameter of 630 μm using a pelletizer.

Comparative Example 6

A catalyst for oxygen-free direct conversion of methane was prepared in the same manner as in Comparative Example 1, with the exception that the amount of Fe(NO$_3$)$_3$.9H$_2$O was changed to 4.1011 g to afford a catalyst (10.0 wt % Fe/SiO$_2$) containing 10.0 wt % of iron supported thereon for oxygen-free direct conversion of methane. The catalyst for oxygen-free direct conversion of methane thus obtained was formed into a pellet-shaped catalyst body having a diameter of 630 μm using a pelletizer.

Comparative Example 7

A catalyst for oxygen-free direct conversion of methane was prepared in the same manner as in Comparative Example 5, with the exception that H-ZSM-5 (Si/Al=23) zeolite was used as the catalyst carrier to afford a catalyst (5 wt % Fe/H-ZSM-5) containing 5 wt % of iron supported thereon for oxygen-free direct conversion of methane. The catalyst for oxygen-free direct conversion of methane thus obtained was formed into a pellet-shaped catalyst body having a diameter of 630 µm using a pelletizer.

Comparative Example 8

A catalyst for oxygen-free direct conversion of methane was prepared in the same manner as in Comparative Example 3, with the exception that quartz particles fused at 1700° C. for 6 hr in ambient air were used as the catalyst carrier to afford a catalyst (0.5 wt % Fe/SiO$_2$) containing 0.5 wt % of iron supported thereon for oxygen-free direct conversion of methane. The catalyst for oxygen-free direct conversion of methane thus obtained was formed into a pellet-shaped catalyst body having a diameter of 630 µm using a pelletizer.

[Test Example 1] Measurement of Free Space $V_{void}$ and $V_{inter}$ of Catalyst The volume $V_R$ of the catalyst-packed portion of the reactor was measured through the packing density of the shaped catalyst body and the weight of the shaped catalyst body present in the reactor, and the intrinsic density, apparent volume $V_A$ and true volume $V_P$ of the catalyst particles were measured using a pycnometer. Moreover, $V_{void}$ was calculated by a random loose packing method, and $V_{inter}$ was calculated by subtracting the true volume $V_P$ of the catalyst particles from the apparent volume $V_A$ of the catalyst particles. The BET specific surface area of the catalysts prepared in Examples 1 to 6 and Comparative Example 8 fell in the range of 1 m$^2$g$^{-1}$ or less, and the BET specific surface area of the catalysts prepared in Comparative Examples 1 to 7 was 400 m$^2$g$^{-1}$ to 450 m$^2$g$^{-1}$. In the initial stage of the reaction, however, carbon deposition occurred rapidly in the interparticle space, and thus the surface area was drastically reduced, indicating that the specific surface area of the catalysts prepared in Comparative Examples 1 to 7 in the reaction stabilization state fell in the range of 1 m$^2$g$^{-1}$ or less. The measured results in the reaction stabilization state are shown in Table 1 below.

TABLE 1

| No. | $V_R$ (ml/g$_{cat.}$) | $V_P$ (ml/g$_{cat.}$) | $V_A$ (ml/g$_{cat.}$) | $V_{free\ space}$ (ml/g$_{cat.}$) | $V_{inter}$ (ml/g$_{cat.}$) | $V_{inter}/V_{void}$ | $(V_{void} + V_{inter})/V_R$ |
|---|---|---|---|---|---|---|---|
| Example 1 | 0.82 | 0.42 | 0.46 | 0.40 | 0.04 | 0.10 | 0.49 |
| Example 2 | 1.13 | 0.42 | 0.63 | 0.70 | 0.20 | 0.40 | 0.62 |
| Example 3 | 0.87 | 0.42 | 0.49 | 0.46 | 0.07 | 0.19 | 0.52 |
| Example 4 | 0.85 | 0.42 | 0.48 | 0.43 | 0.05 | 0.14 | 0.50 |
| Example 5 | 0.82 | 0.42 | 0.46 | 0.40 | 0.04 | 0.11 | 0.49 |
| Example 6 | 0.80 | 0.46 | 0.48 | 0.38 | 0.02 | 0.07 | 0.47 |
| Comparative Example 1 | 2.54 | 0.46 | 1.42 | 2.08 | 0.96 | 0.86 | 0.82 |
| Comparative Example 2 | 2.49 | 0.45 | 1.39 | 2.03 | 0.93 | 0.85 | 0.82 |
| Comparative Example 3 | 2.60 | 0.46 | 1.45 | 2.14 | 0.99 | 0.87 | 0.82 |
| Comparative Example 4 | 2.52 | 0.46 | 1.41 | 2.06 | 0.95 | 0.86 | 0.82 |
| Comparative Example 5 | 2.39 | 0.46 | 1.34 | 1.94 | 0.88 | 0.83 | 0.81 |
| Comparative Example 6 | 1.92 | 0.46 | 1.07 | 1.46 | 0.62 | 0.73 | 0.76 |
| Comparative Example 7 | 1.99 | 0.29 | 1.11 | 1.70 | 0.82 | 0.94 | 0.85 |
| Comparative Example 8 | 1.36 | 0.43 | 0.76 | 0.93 | 0.33 | 0.55 | 0.68 |

As is apparent from Table 1, the true volume $V_P$ of the solid phase of the shaped catalyst body packed in the catalyst-packed portion was 0.42 to 0.46, between which there was no great difference, except Comparative Example 7, but the volume $V_R$ of the catalyst-packed portion varied greatly from 0.80 to 2.60 depending on the preparation method. Moreover, as the Fe content of the catalyst prepared through each preparation method increased, $V_{free\ space}$ gradually decreased. In particular, as the Fe content of the catalyst prepared through each preparation method increased, $V_{inter}/V_{void}$ gradually decreased. When the interparticle space volume $V_{inter}$ of the shaped catalyst body prepared in the Examples was 0.12 or less, it was confirmed that the dispersivity of high-content iron nanoparticles had an important influence on the formation of $V_{free\ space}$ during catalyst fusing. The $V_{free\ space}$ of the catalysts prepared in Examples 1 to 6 was 0.17 to 0.48 times lower than that of the catalysts prepared in Comparative Examples 1 to 7.

[Test Example 2] Oxygen-Free Direct Conversion of Methane 0.6 g of the shaped catalyst body of each of Examples 1 to 6 and Comparative Examples 1 to 7 was packed in a quartz tube reactor (inner diameter: 7 mm). After pretreatment at 960° C. for 30 min in a helium atmosphere, methane and argon were supplied at a volume ratio of 90:10 so that direct conversion of methane was carried out. Here, the gas space velocity was 5000 mlg$_{cat}^{-1}$h$^{-1}$, the retention time of the gas phase except the catalyst-packed portion was 5.49 sec, the reaction temperature was 950° C., the reaction pressure P$_{total}$ was 1 bar, and the methane pressure P$_{CH4}$ was 0.9 bar. After completion of the reaction, the resulting hydrocarbon in a gas phase was analyzed using a Series 6500 GC available from YL Instruments. The gas-phase product was analyzed using a thermal conductivity detector (TCD) connected to a Carboxen 1000 column and two flame ionization detectors (FID) connected respectively to Rt-alumina BOND and RTx-VMS columns. $H_2$, $CH_4$, Ar, $O_2$, CO and $CO_2$ were separated in the Carboxen 1000 column and detected using TCD, and the conversion rates thereof were calculated by the area of $CH_4$ relative to the area of Ar, the internal standard. $C_1$-$C_6$ light hydrocarbons were separated in the Rt-alumina BOND column and detected using FID, and aromatic compounds were separated in the RTx-VMS column and detected using FID. By detecting unreacted gases and products, the carbon balance was maintained at 98% or more. All gases were quantified using standard samples. The coke selectivity was calculated based on [$S_{coke}$=100−Σ product selectivity]. Each catalyst reached the steady state 2 hr after the reaction, and the average methane conversion rate and coke formation rate between 2 hr and 10 hr were calculated as values for the $V_{free\ space}$ of each shaped catalyst body. The results thereof are shown in Table 2 below and in FIGS. 2A and 2B.

[Test Example 3] Oxygen-Free Direct Conversion of Methane

The shaped catalyst body prepared in each of Example 3 and Comparative Examples 3 and 8 was packed in a quartz tube reactor (inner diameter: 7 mm) such that the volume of the catalyst-packed portion was 0.51 ml. After pretreatment at 1020° C. for 30 min in a helium atmosphere, methane and argon were supplied at a volume ratio of 90:10 so that direct conversion of methane was carried out. Here, the gas space velocity was 8727 $mlg_{cat}^{-1}h^{-1}$, the retention time of the gas phase except the catalyst-packed portion was 3.32 sec, the reaction temperature was 1020° C., the reaction pressure $P_{total}$ was 1 bar, and the methane pressure $P_{CH4}$ was 0.9 bar. The methane conversion rate and the hydrocarbon selectivity were measured in the same manner as in Test Example 2. The results thereof are shown in Table 3 below.

TABLE 2

| No. | Methane conversion rate (mmol/h/ml$_{free\ space}$) | Selectivity (%) | | | | | | | | | | |
|---|---|---|---|---|---|---|---|---|---|---|---|---|
| | | Ethane | Ethylene | Acetylene | C3 | C4 | C5 | Benzene | Toluene | Naphthalene | Alkyl aromatics | Coke |
| Example 1 | 11.98 | 8.0 | 36.8 | 11.6 | 9.5 | 10.2 | 1.9 | 6.8 | 1.8 | 1.6 | 2.3 | 9.5 |
| Example 2 | 6.77 | 8.0 | 34.0 | 10.8 | 8.9 | 9.3 | 1.7 | 5.3 | 1.3 | 1.1 | 2.8 | 16.8 |
| Example 3 | 7.65 | 10.3 | 39.5 | 9.7 | 10.0 | 9.7 | 1.5 | 3.4 | 0.8 | 0.4 | 2.1 | 12.6 |
| Example 4 | 9.68 | 9.4 | 34.7 | 9.4 | 8.9 | 8.8 | 1.4 | 3.3 | 0.8 | 0.3 | 1.5 | 21.5 |
| Example 5 | 12.24 | 7.7 | 35.5 | 10.8 | 8.9 | 9.2 | 1.6 | 4.8 | 1.2 | 0.8 | 2.3 | 17.2 |
| Example 6 | 12.97 | 8.0 | 36.8 | 11.1 | 9.1 | 9.2 | 1.7 | 5.6 | 1.4 | 1.2 | 2.5 | 13.4 |
| Comparative Example 1 | 3.95 | 4.8 | 30.6 | 11.2 | 6.7 | 6.3 | 1.2 | 4.6 | 1.1 | 1.0 | 2.0 | 30.5 |
| Comparative Example 2 | 4.06 | 4.4 | 28.6 | 10.5 | 6.1 | 5.7 | 1.0 | 3.8 | 0.9 | 0.6 | 1.3 | 37.1 |
| Comparative Example 3 | 4.33 | 3.9 | 26.3 | 10.3 | 5.8 | 5.8 | 1.1 | 5.0 | 1.2 | 1.1 | 1.8 | 37.7 |
| Comparative Example 4 | 4.47 | 3.9 | 25.5 | 9.3 | 5.5 | 5.1 | 0.9 | 3.4 | 0.8 | 0.5 | 1.1 | 44.0 |
| Comparative Example 5 | 4.28 | 4.6 | 30.3 | 10.9 | 6.3 | 5.9 | 1.0 | 4.7 | 1.1 | 0.8 | 1.9 | 32.5 |
| Comparative Example 6 | 6.64 | 3.6 | 26.8 | 10.5 | 5.6 | 5.3 | 1.0 | 4.6 | 1.1 | 1.2 | 1.8 | 38.5 |
| Comparative Example 7 | 4.03 | 5.6 | 29.7 | 10.8 | 7.5 | 7.4 | 1.4 | 5.3 | 1.4 | 0.9 | 1.9 | 28.1 |

Figure 2A:
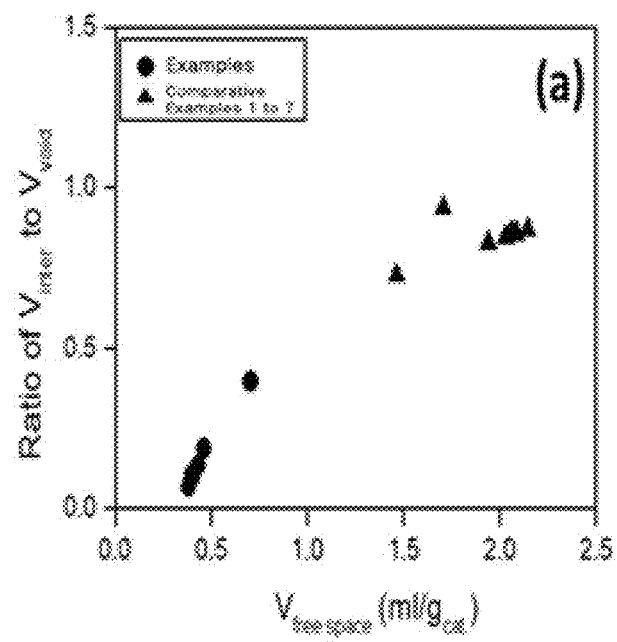
FIGS. 2A and 2B are graphs showing the $V_{inter}/V_{void}$ depending on $V_{free\ space}$ of the catalyst according to an embodiment of the present invention and the methane conversion rate and coke selectivity depending on $V_{free\ space}$ of the catalyst.
Figure 2B:
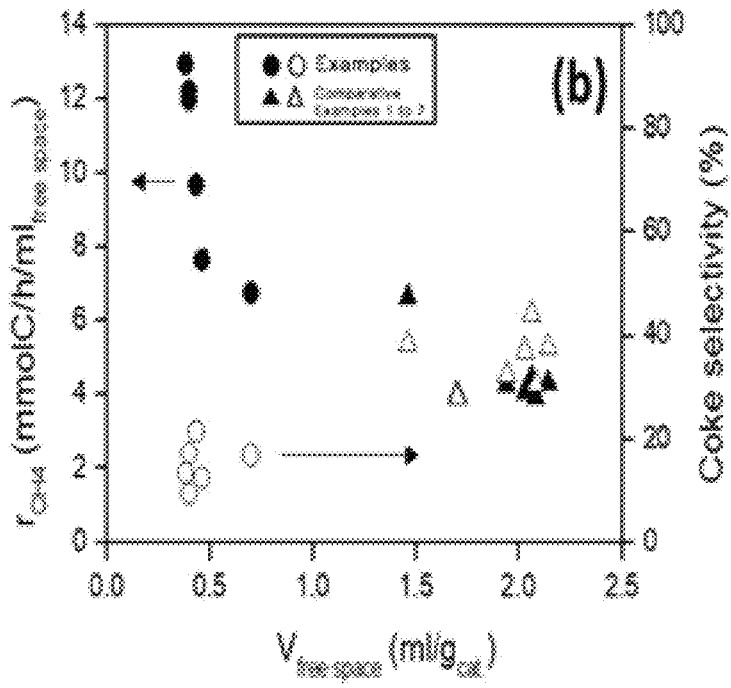

As shown in Table 2 and in FIGS. 2A and 2B, the methane conversion rate was 1.1 to 3.3 times higher in the shaped catalyst bodies of Examples 1 to 6 than in Comparative Examples 1 to 7, but the coke selectivity was 0.2 to 0.8 times lower. Simply put, the shaped catalyst bodies exhibited different activities for oxygen-free direct conversion of methane depending on the preparation process therefor. As the $V_{free\ space}$ of the shaped catalyst bodies prepared in Examples 1 to 6 decreased, the methane conversion rate increased, and as the $V_{free\ space}$ of the shaped catalyst bodies prepared in Examples other than the shaped catalyst body of Example 2 decreased, the coke selectivity increased and then decreased. Meanwhile, in the shaped catalyst body of Example 2, the coke selectivity was relatively high due to the low interaction of Fe and $SiO_2$. Moreover, as the $V_{free\ space}$ of the shaped catalyst body decreased, the $V_{inter}/V_{void}$ ratio decreased, indicating that the space between the shaped catalyst bodies including closed pores and open pores in the packed shaped catalyst bodies plays an important role in the selective conversion of the generated methyl radicals. Particularly, in the shaped catalyst body prepared in Example 1, it was confirmed that the coke selectivity was decreased by 1.8 times compared to the shaped catalyst body prepared in Example 5 in which iron was supported in the same amount.

TABLE 3

| No. | Comparative Example 3 | Comparative Example 8 | Example 3 |
|---|---|---|---|
| Methane conversion rate (mmol/h/ml$_{free\ space}$) | 27.1 | 40.4 | 48.7 |
| Selectivity (%) C2 | 49.5 | 47.6 | 51.3 |
| C3 | 5.1 | 4.5 | 5.3 |
| C4 | 7.0 | 5.8 | 7.0 |
| C5 | 1.5 | 1.4 | 1.6 |
| Aromatics | 26.1 | 29.2 | 33.5 |
| Coke | 10.7 | 11.5 | 1.3 |

As is apparent from Tables 1 and 3, as the $V_{inter}/V_{void}$ of the shaped catalyst body decreased from 0.87 to 0.19, the methane conversion rate was increased from 27.1 to 48.7 mmol/h/ml$_{free\ space}$. The shaped catalyst body prepared in Example 3 exhibited low coke selectivity and high selectivity for aromatics compared to the shaped catalyst bodies prepared in Comparative Examples 3 and 8. Moreover, the shaped catalyst body prepared in Example 3 exhibited slightly high $C_2$ product (ethane, ethylene, acetylene) selectivity compared to the shaped catalyst bodies prepared in Comparative Examples 3 and 8.

[Test Example 4] Measurement of Catalyst Stability 0.6 g of the shaped catalyst body prepared in Example 3 was packed in a quartz tube reactor (inner diameter: 7 mm). After pretreatment at 1020° C. for 30 min in a helium atmosphere, methane and argon were supplied at a volume ratio of 90:10 so that direct conversion of methane was carried out. Here, the gas space velocity was 8727 $mlg_{cat}^{-1}h^{-1}$, the retention time of the gas phase except the catalyst-packed portion was 3.32 sec, the reaction temperature was 1020° C., the reaction pressure $P_{total}$ was 1 bar, and the methane pressure $P_{CH4}$ was 0.9 bar. The methane conversion rate and the hydrocarbon selectivity were measured in the same manner as in Test Example 2. The results thereof are shown in FIG. 3.

Figure 3:
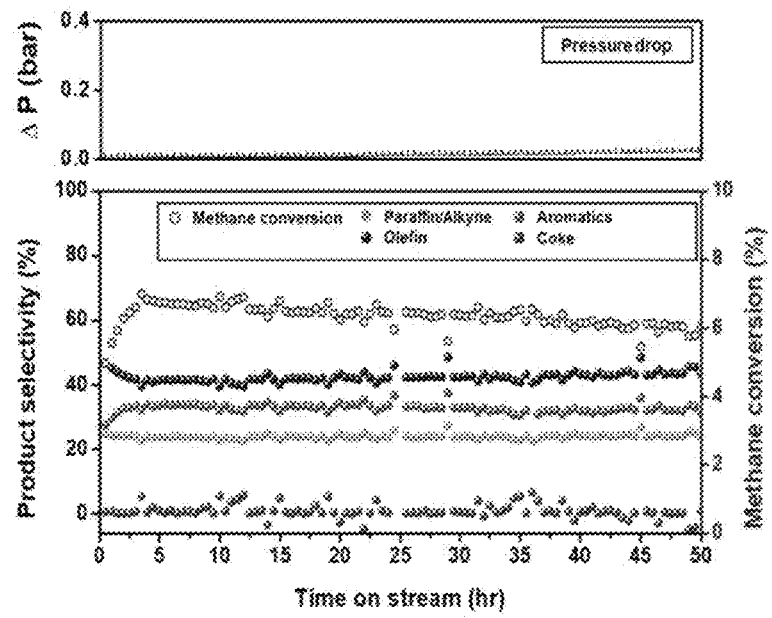
FIG. 3 is a graph showing the product selectivity and the methane conversion rate depending on the catalytic reaction time at a reaction temperature of 1020° C. according to an embodiment of the present invention.
Figure 3:
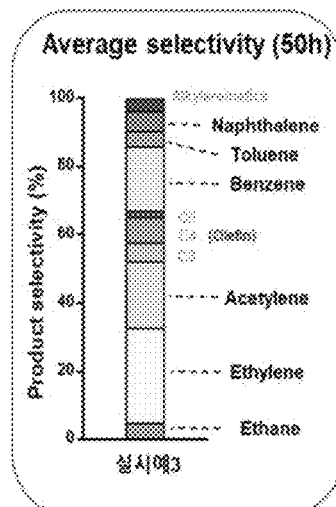

As shown in FIG. 3, the shaped catalyst body prepared in Example 3 exhibited a methane conversion rate reduction of about 1% for 50 hr. Almost no coke selectivity was observed during the reaction time, indicating that most of the methane was converted into hydrocarbons. The hydrocarbon selectivity did not show a great difference depending on the reaction time. Here, the C2-C5 olefin selectivity was about 42.6% and the selectivity for aromatics was about 32.9%. The selectivity of ethane as the C2 product was about 4.6%, the ethylene selectivity was about 28.0%, and the acetylene selectivity was 19.4%. The selectivity of benzene as the aromatic compound was about 18.9%, the toluene selectivity was about 4.3%, and the naphthalene selectivity was about 6.2%. No pressure drop occurred when the reaction was carried out using the shaped catalyst body prepared in Example 3.

All simple modifications or variations of the present invention that may be easily performed by those skilled in the art fall within the scope of the present invention.

What is claimed is:

1. A catalyst for oxygen-free direct conversion of methane, which is granulated and packed in a shaped catalyst body form in a reactor for oxygen-free direct conversion of methane,
wherein the catalyst satisfies Mathematical Formula 1 below:

$(V_{inter}/V_{void}) \le 0.4$     [Mathematical Formula 1]

in Mathematical Formula 1, $V_{void}$ is $V_R - V_A$, $V_R$ is a volume of a catalyst-packed portion in the reactor, and $V_A$ is an apparent volume of the shaped catalyst body packed in the catalyst-packed portion, and $V_{inter}$ is an interparticle space volume of the shaped catalyst body packed in the catalyst-packed portion, and
wherein the catalyst comprises:
a catalyst carrier comprising silicon oxide; and
iron dispersed in a monoatomic form on the catalyst carrier.

2. The catalyst of claim 1, wherein a ratio $[(V_{void}+V_{inter})/V_R]$ of $V_{void}$ and $V_{inter}$ to $V_R$ of the catalyst is 0.7 or less.

3. The catalyst of claim 1, wherein a sum of $V_{void}$ and $V_{inter}$ of the catalyst is 0.7 $ml/g_{cata.}$ or less.

4. The catalyst of claim 1, wherein the $V_{inter}$ of the catalyst is 0.2 $ml/g_{cata.}$ or less.

5. The catalyst of claim 1, wherein an amount of iron that is supported is 0.1 wt % to 10.0 wt % based on a total weight of the catalyst.

6. The catalyst of claim 1, wherein the catalyst carrier is in a crystalline molten state.

7. The catalyst of claim 1, wherein the is decreased through repeated fusing and solidification.

8. A method of converting methane, comprising:
reacting methane in an anaerobic or oxygen-free atmosphere using the catalyst of claim 1.

9. The method of claim 8, wherein the reacting is carried out at a temperature of 950° C. to 1100° C.

* * * * *